(12) United States Patent
Ludwig

(10) Patent No.: US 7,562,776 B1
(45) Date of Patent: Jul. 21, 2009

(54) SLIDE HOLDER FOR STAINING SPECIMENS DISPOSED ON MICROSCOPE SLIDES

(76) Inventor: Melynda Bautista Ludwig, 20650 Via Roja, Yorba Linda, CA (US) 92886

( * ) Notice: Subject to any disclaimer, the term of this patent is extended or adjusted under 35 U.S.C. 154(b) by 631 days.

(21) Appl. No.: 11/162,869

(22) Filed: Sep. 27, 2005

(51) Int. Cl.
*B65D 85/48* (2006.01)
(52) U.S. Cl. .................. 206/456; 206/438; 206/775
(58) Field of Classification Search ............... 206/456, 206/316.1, 775, 486, 438
See application file for complete search history.

(56) References Cited

U.S. PATENT DOCUMENTS

| | | | | |
|---|---|---|---|---|
| 1,234,641 | A | * 7/1917 | Dickson | 396/642 |
| 2,058,128 | A | * 10/1936 | Brubach | 24/545 |
| 2,082,876 | A | * 6/1937 | Davis | 396/651 |
| 2,402,765 | A | * 6/1946 | Millman | 396/651 |
| 3,081,870 | A | * 3/1963 | Piettner | 206/456 |
| 4,523,826 | A | 6/1985 | Gunduz et al. | |
| 4,565,073 | A | * 1/1986 | Lavender | 62/373 |
| 4,589,551 | A | 5/1986 | Hellon | |
| 4,635,790 | A | 1/1987 | Jackson et al. | |
| 4,635,791 | A | 1/1987 | Jackson et al. | |
| 4,960,224 | A | 10/1990 | Boenisch | |
| 5,021,218 | A | * 6/1991 | Davis et al. | 422/104 |
| 5,588,531 | A | * 12/1996 | Yoshida et al. | 206/454 |
| 6,239,906 | B1 | * 5/2001 | Lorincz | 359/396 |
| 2002/0008045 | A1 | 1/2002 | Guyot et al. | |
| 2002/0096447 | A1 | 7/2002 | Lafond et al. | |
| 2003/0111373 | A1 | * 6/2003 | Chouinard et al. | 206/456 |
| 2003/0226781 | A1 | 12/2003 | Liao | |
| 2004/0031712 | A1 | 2/2004 | Maxim et al. | |

FOREIGN PATENT DOCUMENTS

| | | |
|---|---|---|
| CA | 2326811 | 11/2000 |
| CA | 2301968 | 9/2001 |
| WO | WO 0196193 A2 | 12/2001 |
| WO | WO 0196193 A3 | 12/2001 |
| WO | WO 02099503 A1 | 12/2002 |

OTHER PUBLICATIONS http://www.tedpella.com/histo_html/slidebox.htm retrieved from http://www.archive.org for Jun. 22, 2003.
http://www.laddresearch.com/General_Catalog/Chapter_13/Microscope_Slides_Accessorie/microscope_slides_accessorie.html retrieved from http://www.archive.org for Jan. 25, 2003.
http://www.emsdiasum.com/ems/histology/staining.html retrieved from http://www.archive.org for Jun. 17, 2003.

* cited by examiner

*Primary Examiner*—J. Gregory Pickett
*Assistant Examiner*—Jenine M Pagan
(74) *Attorney, Agent, or Firm*—Freedman Patent; Immanuel Freedman

(57) ABSTRACT

A slide holder for staining specimens disposed on microscope slides including a body member further including a front wall having at least one hole, a first side wall connected to the front wall, a second side wall connected to the front wall, a back wall connected to the first side wall and connected to the second side wall and, a bottom wall connected to the front wall, the first side wall, the second side wall and the front wall, the bottom wall having at least one hole. Guide means for maintaining a spaced relationship between the faces of each of a plurality of slides inserted into the guide means, are disposed in the body member. An optional handle is affixed to the body member by a tack weld or the like.

6 Claims, 4 Drawing Sheets

Rib Detail

SLIDE HOLDER FOR STAINING SPECIMENS DISPOSED ON MICROSCOPE SLIDES

FIELD OF THE INVENTION

This invention relates to slide holders for staining specimens disposed on microscope slides.

DETAILED DESCRIPTION OF PRESENTLY PREFERRED EMBODIMENTS

Figure 1:
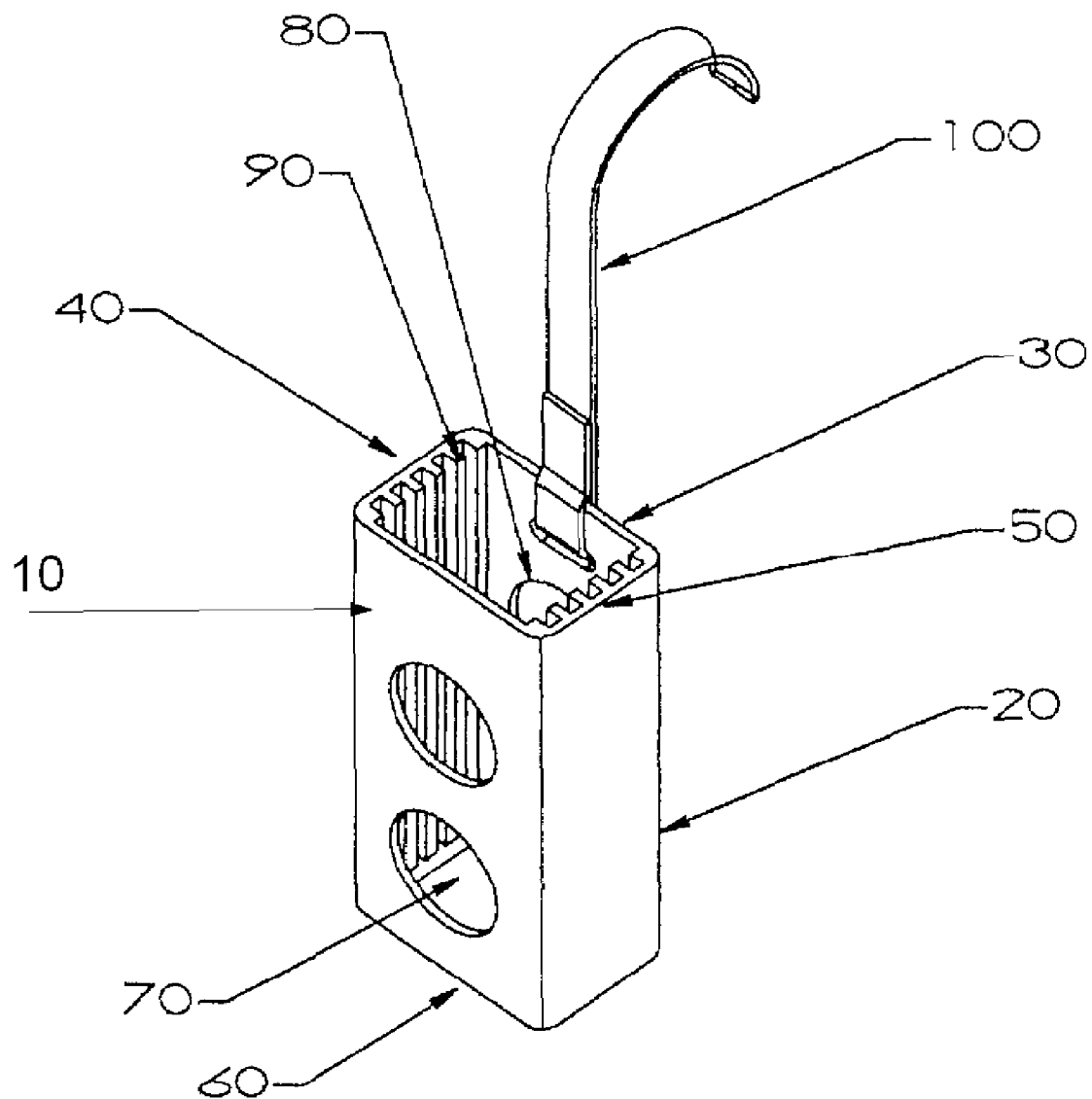
FIG. 1 illustrates an exemplary isometric view of the slide holder.

Referring to FIG. 1, the presently preferred embodiment of the slide holder comprises a substantially rectangular body member 20 disposed with its longitudinal axis substantially vertical. In an alternative embodiment, the body member 20 may be disposed with its longitudinal axis substantially horizontal. The body member 20 comprises a front wall 10, first side wall 40 connected to the front wall 10, a back wall 30 connected to the first side wall 40, a second side wall 50 connected to the back wall 30 and a bottom wall 60 connected to the back wall 30, the first side wall 40 and the second side wall 50. The front wall 10 and back wall 30 each have at least one hole 80 and the bottom wall has at least one hole 70. In an alternative embodiment, the front wall 10 may be open. In yet another alternative embodiment, the back wall 30 may be open. The front wall 10, the first side wall 40, the second side wall 50 and the bottom wall 60 are fabricated with guide means 90, such as ribs, slots, guides or the like. An optional handle 100 is affixed to the body member 20 and the optional handle 100 is preferably affixed to the back wall 30.

Figure 2:
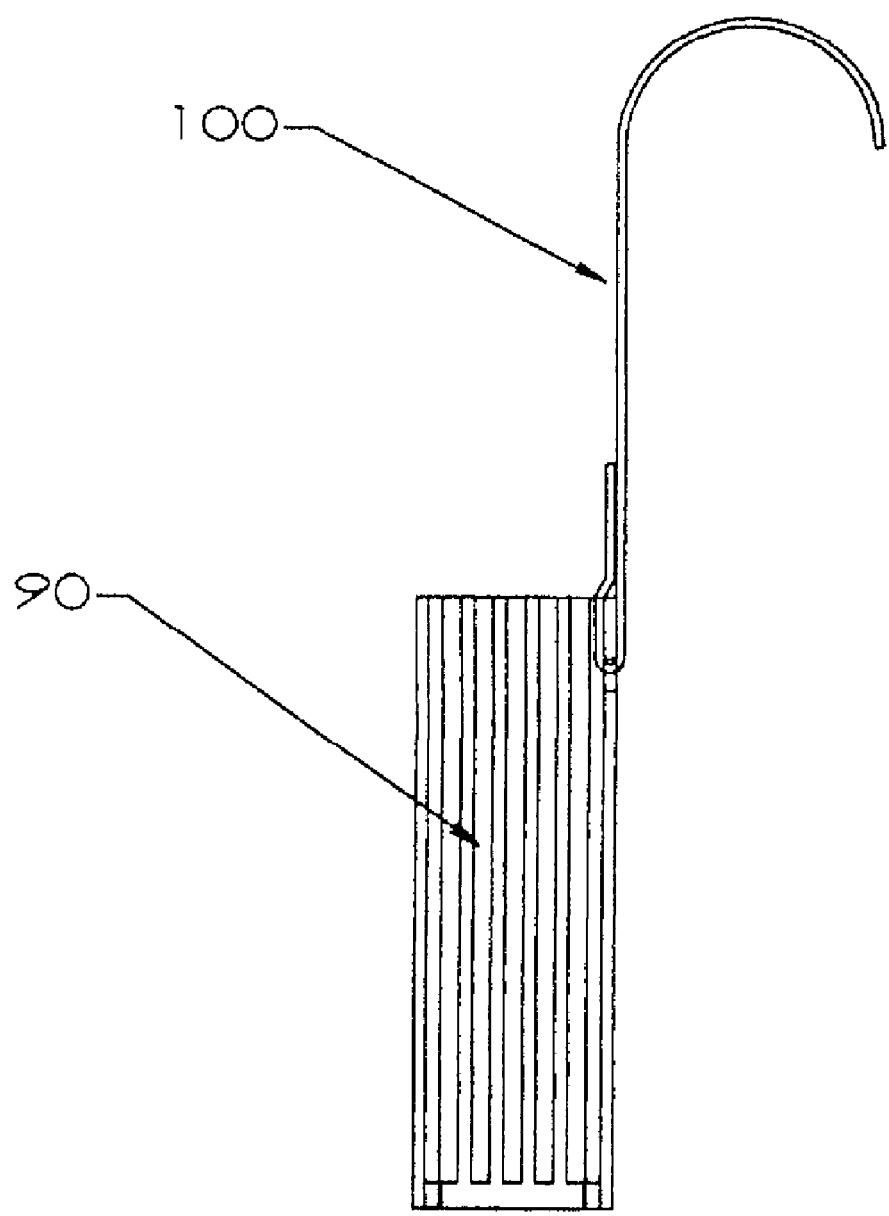
FIG. 2 illustrates an exemplary side view of the slide holder.

FIG. 2 shows a side view of the slide holder including optional handle 100, particularly illustrating the guide means 90, such as ribs, slots, guides or the like. In the presently preferred embodiment, the optional handle 100 is preferably affixed to the back wall 30 by a tack weld.

Figure 3:
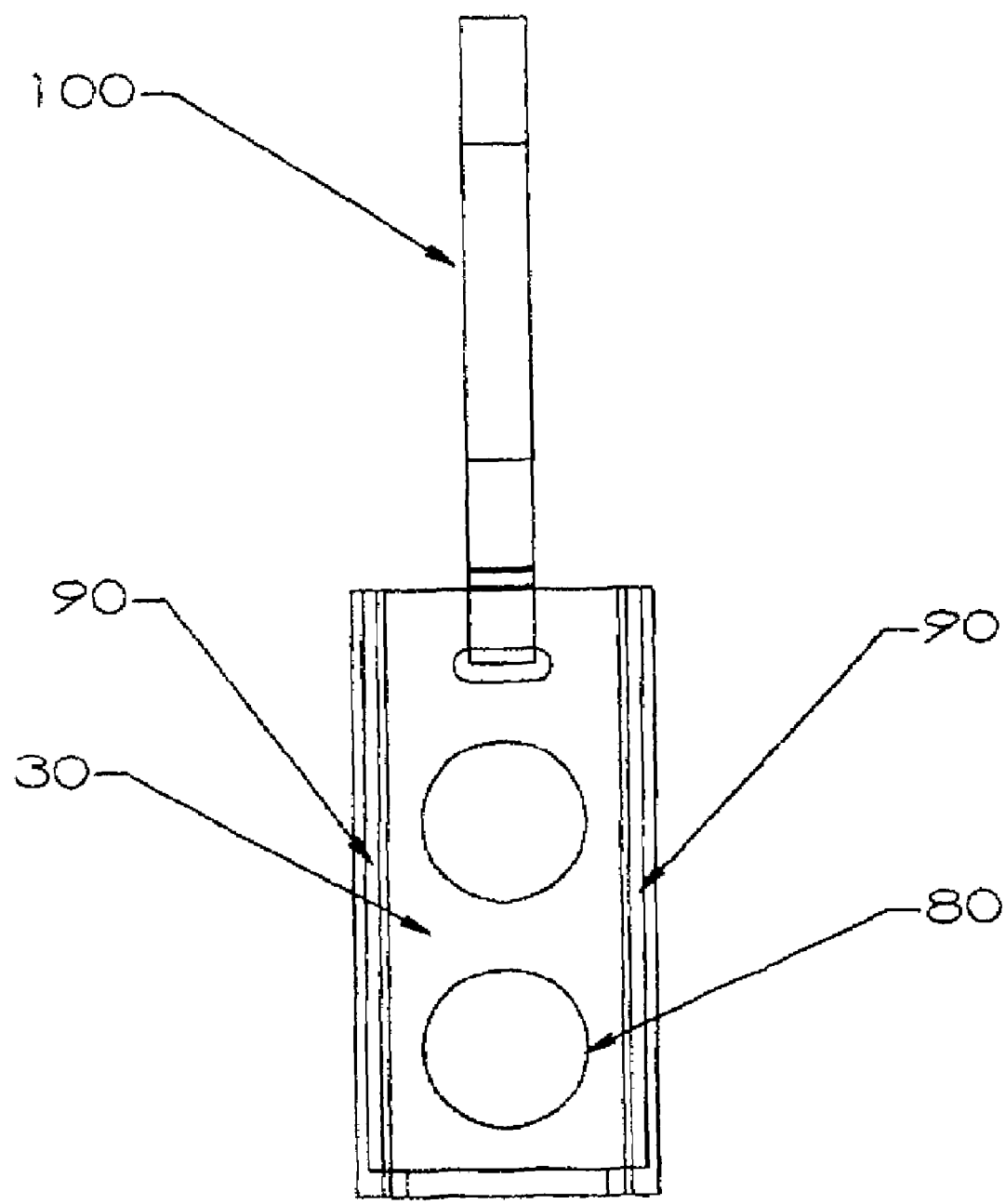
FIG. 3 illustrates an exemplary back view of the slide holder.

FIG. 3 shows a back view of the slide holder including optional handle 100, illustrating the guide means 90 and the back wall 30 having at least one hole 80.

Figure 4:
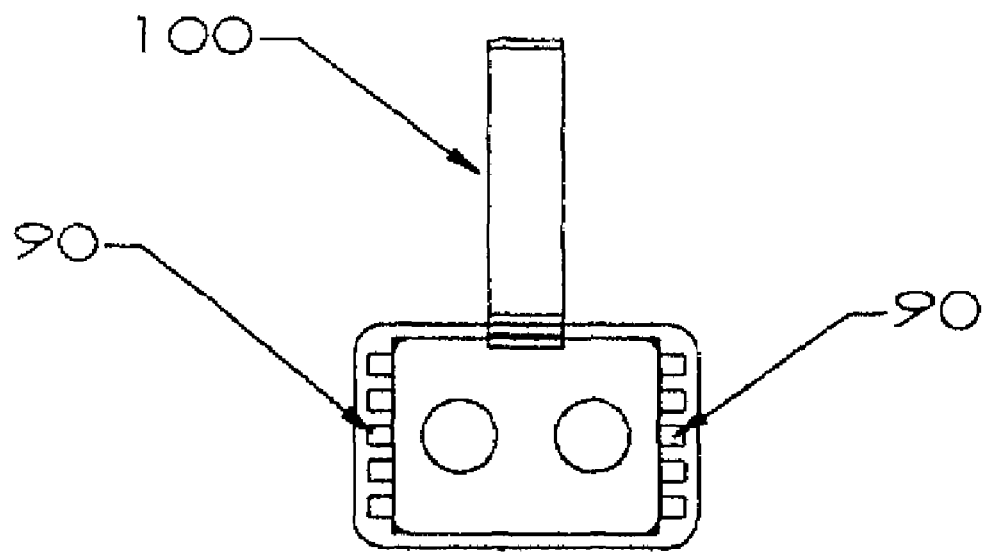
FIG. 4 illustrates an exemplary top view of the slide holder.

FIG. 4 shows a top view of the slide holder including optional handle 100, particularly illustrating the bottom wall 60 having at least one hole 70, together with guide means 90.

Figure 5:
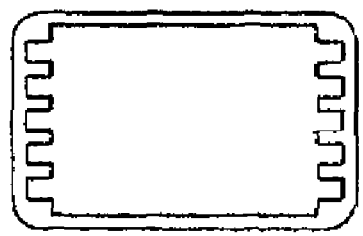
FIG. 5 illustrates exemplary details inside the slide holder.

FIG. 5 shows details of the guide means 90 in the presently preferred embodiment in which the guide means 90 are preferably ribs.

In the presently preferred embodiment, the body member 20 is fabricated from a plastic material and the optional handle 100 is fabricated from a metal material. In alternative embodiments, the body member 20 and optional handle 100 may each be fabricated from a plastic material, a metal material, or any suitable material within the skill in the art. In the presently preferred embodiment, the plastic material is at least one of polypropylene, nylon, polyethylene, fiber glass reinforced plastic and poly vinyl chloride (PVC), or the like and, the metal material is at least one of stainless steel, chrome alloy steel, aluminum $T_6T_4$, or the like. In the presently preferred embodiment, the optional handle 100 is affixed to the body member 20 by a tack weld, or the like.

In the presently preferred embodiment, to accommodate currently available microscope slides, the body member 20 is of height about 2.375 inch and the back wall 30 has three holes 80. Two of the holes 80 are substantially circular of diameter about 0.625 inch, with centers substantially disposed on the vertical midline of the back wall 30 at depth 0.9 and 1.8 inch, respectively. The third hole 80 is of substantially horizontal oval shape, of height about 0.125 inch and center substantially disposed on the vertical midline of the back wall 30 at depth about 0.3 inch.

In the presently preferred embodiment, the optional handle 100 is fabricated to a height of about 2.24 inch with a linear portion disposed substantially vertically and an arcuate portion with radius of curvature about 0.5 inch. The optional handle 100 is affixed to the back wall 30 by a tack weld or the like, extending about 0.375 inch above the body member 20.

In the presently preferred embodiment, the bottom wall 60 has two holes 70. Each hole is substantially circular, of diameter about 0.063 inch and the centers are substantially equidistant and substantially disposed on the horizontal midline of the bottom wall 60.

In the presently preferred embodiment, the guide means 90, such as ribs, slots, guides or the like, are corrugated of width about 0.07 inch to accommodate currently available microscope slides and the guide means 90 are spaced by about 0.05 inch to substantially prevent contact between the faces of successively inserted slides and likewise substantially permit contact between the inserted slides and side walls 40 and 50.

In operation, microscope slides containing specimens disposed in specimen zones are inserted into the guide means 90 such that the specimen zones are substantially completely disposed within the body member 20 when the slides are fully inserted. In an exemplary embodiment, the specimens comprise biological specimens. The slide holder, optionally held by the optional handle 100 is then submerged in a staining liquid to a depth sufficient to substantially completely cover the specimen zones and then withdrawn from the staining liquid when the staining process is substantially complete. The slide holder is designed to provide advantages including that microscope slides inserted into the guide means will substantially remain inside the slide holder when the slide holder is submerged in a staining liquid, the staining liquid will maintain substantial contact with microscope slides inserted into the slide holder and, substantially all the staining liquid will drain from the slide holder when the slide holder is withdrawn from the staining liquid.

Whereas particular embodiments of the present invention have been described above for purposes of illustration, it will be evident to those skilled in the art that numerous variations of the details may be made with departing from the invention as defined by the appended claims.

What is claimed is:

1. An apparatus, comprising:
   a substantially rectangular body member, comprising
   a substantially planar front wall,
   a substantially planar first side wall connected to said front wall,
   a substantially planar second side wall connected to said front wall,
   a substantially planar back wall connected to said first side wall and said second side wall, and
   a substantially planar bottom wall connected to said front wall, said back wall, said first side wall and said second side wall, said front wall having at least one hole, said back wall having at least one hole and, said bottom wall having at least one hole;

a plurality of substantially rigid microscope slides having substantially rectangular parallelepiped shape;

a plurality of specimens affixed to a plurality of specimen zones disposed on one of the faces of each of the plurality of microscope slides;

a plurality of ribs for maintaining a spaced relationship between said faces of each of the plurality of slides and maintaining a spaced relationship between said plurality of slides, said front wall, said first side wall, said second side wall, said back wall and said bottom wall, when said plurality of slides is substantially fully inserted in said plurality of ribs, wherein each rib has breadth substantially equal to the breadth of each of the plurality of slides and the spacing between said ribs is substantially equal to the height of each of the plurality of slides, said plurality of ribs being disposed in said body member, wherein said body member has a height sufficient to cause said plurality of specimen zones to be substantially completely disposed within said body member when said plurality of slides is substantially fully inserted in said body member and said body member has a cross-sectional area sufficient to receive said plurality of slides, said apparatus adapted to stain with a staining liquid intended to stain biological specimens the plurality of specimens affixed to a plurality of specimen zones disposed on one of the faces of each of said plurality of microscope slides when said plurality of microscope slides is substantially inserted into said body member.

2. An apparatus as claimed in claim 1, wherein said bottom wall has at least one hole of size such that said bottom wall is substantially open.

3. An apparatus as claimed in claim 1, wherein said plurality of ribs engages the side edges of said plurality of slides when said plurality of slides is inserted in said plurality of ribs.

4. An apparatus as claimed in claim 1, wherein the inserted ends of said plurality of slides are substantially in contact with said bottom wall when said plurality of slides is fully inserted in said plurality of ribs.

5. An apparatus as claimed in claim 1, wherein said plurality of ribs substantially permits engagement of the side edges of said plurality of slides with said front wall, said first side wall, said second side wall and said back wall and substantially prevent contact of said plurality of specimen zones said front wall, said first side wall, said second side wall and said back wall.

6. An apparatus as claimed in claim 1 wherein each of said plurality of ribs substantially has width about 2.375 inches and said plurality of ribs is substantially spaced apart by about 0.07 inch.

* * * * *